United States Patent [19]

Mano

[11] 4,321,711
[45] Mar. 30, 1982

[54] VASCULAR PROSTHESIS
[75] Inventor: Hiroshi Mano, Osaka, Japan
[73] Assignee: Sumitomo Electric Industries, Ltd., Osaka, Japan
[21] Appl. No.: 84,323
[22] Filed: Oct. 12, 1979
[30] Foreign Application Priority Data
Oct. 18, 1978 [JP] Japan ................................ 53/128695
[51] Int. Cl.³ .............................................. A61F 1/24
[52] U.S. Cl. ................................................. 3/1.4; 3/1
[58] Field of Search ........................................ 3/1.4, 1
[56] References Cited
U.S. PATENT DOCUMENTS
3,279,996 10/1966 Long, Jr. et al. ...................... 3/1 X
3,425,418 2/1969 Chvapil et al. ....................... 3/1.4 X
3,512,183 5/1970 Sharp et al. .......................... 3/1.4 X
3,585,647 6/1971 Gajewski et al. ......................... 3/1.4
3,688,317 9/1972 Kurtz .................................... 3/1.4
3,914,802 10/1975 Reick .................................... 3/1.4
4,011,861 3/1977 Enger ........................... 128/419 P X
4,208,745 6/1980 Okita ..................................... 3/1 X Primary Examiner—Clifford D. Crowder
Attorney, Agent, or Firm—Sughrue, Mion, Zinn, Macpeak & Seas

[57] ABSTRACT

A vascular prosthesis comprising a porous tubing of polytetrafluoroethylene containing an anti-coagulant substance and bonded to its outside surface a porous elastomer coating containing substance which counteracts the anti-coagulant substance is disclosed.

17 Claims, 1 Drawing Figure

VASCULAR PROSTHESIS

BACKGROUND OF THE INVENTION

1. Field of the Invention

This invention relates to a vascular prosthesis composed of a porous tubing of polytetrafluoroethylene (to be abbreviated "PTFE"), and aims at increasing the anti-coagulating property of its inner surface, preventing bleeding, and is directed to increasing the strength of the tubing and improving the ability of its outside surface to connect with the tissues of a patient.

2. Description of the Prior Art

Many reports have been made heretofore to show that a porous tubing of PTFE produced by a stretching method can be clinically used as a vascular prosthesis. Such a prosthesis is regarded as better than conventional vascular prosthesis made of knitted or woven fabrics. A PTFE tubing which has been subjected to a stretching treatment has a microstructure composed of very fine fibers and nodes connected to one another by these fibers. The diameters of the fibers vary depending on stretching conditions, but can be made much smaller than those of the fibers of the knitted or woven fabrics mentioned above. Moreover, since the pore diameter and porosity of the tubing can be varied freely, when it is used as an artificial vessel, it is pliable and scarcely permits formation of thrombus. The tubing also shows good formation of a neointima on its inner surface without any appreciable adverse effect on the surrounding tissues. Thus, the stretched PTFE tubing is regarded as one of the best vascular prostheses.

However, the porous PTFE tubing of PTFE produced by stretching is not completely free from formation of thrombus and still has room for improvement. The stretched PTFE tubing also has the disadvantage that when it is used as a vascular prosthesis and joined with the living body, the needle or suture tends to tear the tubing. Moreover, it is difficult for natural occlusion of suture holes to occur based on the elasticity of the porous PTFE tubing alone, and bleeding from the suture holes is sometimes noted after the junction operation. Another problem is the low ability of the outside surface of the porous PTFE tubing to connect with the surrounding tissues of a patient.

The present invention offers a solution to these problems.

SUMMARY OF THE INVENTION

It is an object of this invention to provide a vascular prosthesis which is free from the formation of thrombus and tearing and permits natural occlusion of suture holes.

According to this invention, there is provided a vascular prosthesis comprising a porous tubing of polytetrafluoroethylene containing an anti-coagulant substance and bonded to its outside surface, a porous elastomer coating containing a substance which counteracts the anti-coagulant.

BRIEF DESCRIPTION OF THE INVENTION

FIGURE 1 is a side view of the vascular prosthesis of this invention showing the essential elements thereof. Said prosthesis is provided with a body of porous PTFE 1, containing an anti-coagulant substance, which body is provided and bonded with an elastomeric coating 2 upon its outer surface, containing a substance which counteracts the anti-coagulant contained in the PTFE body.

DETAILED DESCRIPTION OF THE INVENTION

Figure 1:
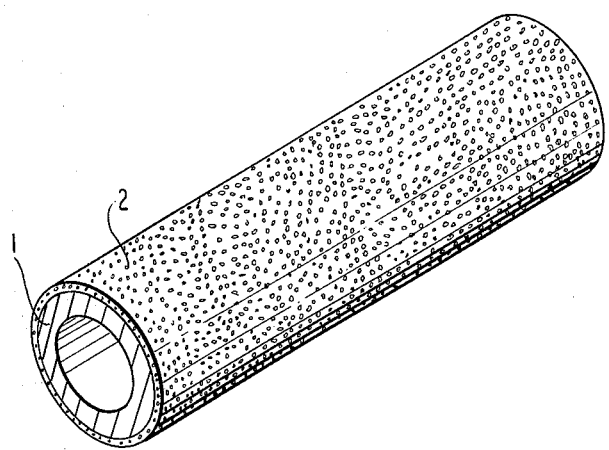

Since the vascular prosthesis of this invention contains an anti-coagulant substance, thrombi do not form on its inside surface. The provision of the porous elastomer coating obviates the problem of tube tearing, and suture holes are occluded under the elasticity of the coating. Should bleeding occur in the sutured areas, it will be stopped by the counteracting substance contained in the coated portion. This substance can further prevent bleeding incident to the leakage of the anti-coagulant substance. In addition, the ability of the tubing to connect with the surrounding tissues of a patient is increased by the porous elastomer coating.

The porous tubing of PTFE in accordance with this invention is produced by the method described in Japanese Patent Publication No. 13560/67 and, e.g., U.S. Pat. Nos. 3,962,153 and 3,953,566. A liquid lubricant is mixed with an unsintered powder of polytetrafluoroethylene, and the mixture is extruded into a tubular form by a ram-type extruder. The PTFE used in this invention preferably has a molecular weight of $10^6$ to $10^7$. The tubing is stretched at least monoaxially after the liquid lubricant is optionally removed from it. The tubing is then heated at a temperature above about 327° C. which is the sintering temperature while fixing it in place to avoid shrinkage. Thus, the stretched and expanded structure is fixed to give a tubing having increased strength. The resulting porous PTFE tubing has a microstructure composed of very fine fibers and nodes connected to one another by these fibers. Because the diameters and lengths of these fibers and the sizes and number of the nodes can be varied depending upon the stretching and sintering conditions, the pore diameter and porosity of the resulting porous tubing can be freely determined. It has been clinically confirmed that as a vascular prosthesis it suitably has an average pore diameter of about 2 μm to about 100 μm, a porosity of at least about 70%, and a wall thickness of about 0.3 to about 1.0 mm.

In a preferred form of the microstructure of the porous PTFE tubing used in this invention, the fibers are distributed not unidirectionally but radially. This fibrous structure is obtained by biaxially stretching the PTFE tubing, namely by stretching it in the axial direction and expanding its diameter. Expansion of its diameter can be achieved by reducing the pressure on the outside surface of the tubing, or applying pressure to its inside surface, or simultaneously performing these two procedures. Alternatively, the diameter of the tubing may be mechanically enlarged by passing an article of a suitable configuration through the inside of the tubing. Stretching of the tubing in the axial direction and expansion of its diameter are carried out simultaneously or successively, or may be carried out simultaneously with the final sintering step. The porous PTFE tubing obtained by the biaxial stretching method is more pliable and less prone to longitudinal tearing than a porous PTFE tubing stretched only in the axial direction, because the fibers are distributed not only in the axial direction but radially in all directions. However, for use as a vascular prosthesis, it still leaves room for improvement.

The porous elastomer coating is used in this invention for the purpose of preventing tearing of the tubing, stopping bleeding by occlusion of suture holes by the elastomer, and increasing the ability of the tubing to connect with the surrounding tissues of a patient.

Any elastomer can be used in this invention which does not harm the body. Examples are fluorine rubber, silicone rubber, urethane rubber, acrylic rubber, and natural rubber. Usually, elastomers are used in the crosslinked state, and in this invention, too, the elastomers are used preferably in the crosslinked state in order to prevent their deterioration in the living body.

For use as a vascular prosthesis, the suitable average poor diameter of the porous elastomer coating is from about 10 $\mu$m to about 500 $\mu$m, a sufficient thickness of the coating is equal to, or smaller than, the wall thickness of the porous PTFE tubing, i.e., about 20 $\mu$m to about 500 $\mu$m, and the elastomer has a porosity of about 50% to about 90%.

A porous coating of the elastomer can be formed on the outside surface of the porous PTFE tubing by a variety of methods including a method comprising wrapping a separately prepared porous sheet of the elastomer about the outside surface of the tubing and bonding it, a method comprising coating a solution of an elastomer compound containing a blowing agent on the outside surface of the tubing and then decomposing the blowing agent, a method comprising coating a solution of an elastomer compound having a soluble substance dispersed therein on the outside surface of the tubing, and dissolving the soluble substance to form a porous structure, a method comprising dissolving an elastomer compound in a mixture of a solvent and a nonsolvent, coating the solution on the outside surface of the tubing, and drying the coating to render it porous, or a method comprising coating a solution of an elastomer compound on the outside surface of the tubing, and removing the residual solvent by dipping the coated tubing in a nonsolvent bath or heating it to a temperature above the boiling point of the solvent, thereby to render the coating porous.

In particular, a method for forming a porous coating of an elastomer, which comprises coating the outside surface of porous tubing of PTFE with a solution of an elastomer compound or a liquid elastomer compound, and before drying the elastomer coating, applying a negative pressure to the inside wall of the porous tubing with a gas or liquid whereupon passing through the elastomer the gas or liquid foams the elastomer and thus renders the coating porous has been found to be most suitable for the object of this invention. The term "negative pressure" as used herein denotes a pressure greater on the inside wall than the outside wall of the tubing. A pressure of about 0.05 to 1 kg/cm$^2$ is usually applied to the inside wall of the tubing. A preferred viscosity of the elastomeric coating before foaming is from about 100 to about 5,000 c.p. at 25° C.

The elastomer compound, as used herein, denotes a mixture of the elastomer with a crosslinking agent, etc.

In the resulting structure comprising the porous PTFE tubing and the porous elastomer coating bonded to its outside surface, the porous PTFE tubing portion contains an anti-coagulant substance, and the porous elastomer coating contains a substance which counteracts the anti-coagulant substance.

The anti-coagulant substance serves to increase the anti-coagulating property of the inside surface of the porous PTFE tubing, and to provide an artificial vessel which shows a high patency rate without the formation of thrombus. It is provided within the pores of the porous PTFE tubing. The anti-coagulant substance may be provided uniformly over all the pores of the porous PTFE tubing, but is preferably only on the inside surface of the tubing.

Examples of the anti-coagulant substance include polysaccharide sulfates such as heparin, its derivatives, chondroitin sulfate, charonin sulfate, and organic acids such as citric acid. Heparin sodium is most effective and is most easily available.

To provide the anti-coagulant substance in the pores of the porous PTFE tubing, the tubing is dipped in a solution of the anti-coagulant substance and dried. Or a polymeric gel or the like is provided within the pores, and the anti-coagulating substance is held therein. The latter method generally gives better results with regard to the durability of the anti-coagulating property of the substance. Examples of materials for the polymeric gel include synthetic water-soluble polymers such as polyvinyl alcohol, polyethylene oxide, polyethylene glycol, polyvinyl pyrrolidone and polyacrylic acid, and natural hydrophilic polymers such as cellulose derivatives, pectin, and alginic acid.

The anti-coagulant substance may be held in the PTFE tubing by mixing it with a solution of the above polymer, impregnating the pores of the porous PTFE tubing with the solution, and gelling the solution by a method suitable for the respective polymer (the term "gelling" includes cross-linking). Another effective method comprising impregnating the pores of the PTFE tubing with a solution of a polymeric amine such as polyethyleneimine or polyvinyl amine, cross-linking the polymer, quaternizing it, and contacting the product with a solution of heparin sodium or the like to bond heparin ionically as described in Japanese Patent Application (OPI) No. 13694/1979 (The term "OPI" as used herein refers to a "published unexamined Japanese patent application") corresponding to U.S. patent application Ser. No. 921,680, filed July 3, 1978, now U.S. Pat. No. 4,229,838. It has already been found that ionically bonded heparin or the like has a better anti-coagulating effect than that bonded by other methods, and its effect lasts for an extended period of time. In the present invention, too, this bonding method has been found to be most effective.

When a hydrophilic polymer is used to hold the anti-coagulant substance, it results in the formation of a hydrophilic portion on the surface of PTFE which is highly water-repellent, and therefore, the product also shows an anti-coagulant effect attributed to a balanced combination of water repellency and hydrophilicity. Coupled with the activity of the anti-coagulant substance, this provides a vascular prosthesis having superior properties. A suitable concentration for the polymeric solution is usually not more than 10 wt%, and the suitable concentration for the anti-coagulant substance is in the range of about 0.2 to 5 wt% (in the case of heparin sodium). Conveniently, impregnation is performed only on the inside surface of the porous PTFE tubing such that the anti-coagulating property of only the inside surface is increased.

The counteracting substance for the anti-coagulant substance in this invention is contained in the porous elastomer coating portion, and serves to stop bleeding. The counteracting substance includes a substance which acts in a way opposite to the anti-coagulant substance on the inside surface of the tubing, and a substance which reduces or nullifies the function of the anti-coagulant. Examples of the counteracting substance are inorganic or organic coagulating substances such as silica, alumina, carbon black, or activated carbon, and antagonistic agents against anti-coagulant substances. Typical examples of antagonistic agents against heparin are protamine, and its derivatives such as protamine sulfate and protamine zinc.

Such a counteracting substance may be incorporated into the elastomer as a filler, or provided in the pores of the porous elastomer coating. When it is mixed with the elastomer, its amount is sufficiently up to 10% by weight based on the weight of the elastomer. When it is provided in the pores of the elastomer coating, its amount may be small. Desirably, it is used in an amount larger than that which is required to nullify the entire amount of the anti-coagulant substance.

The provision of the coagulating substance in the pores of the elastomer coating is suitably achieved by impregnating the porous elastomer with a dispersion of coagulating substance and drying the impregnated elastomer. It has been confirmed that the coagulating substance present in the pores of the elastomer will not come out. In order to fix the coagulating substance onto the inner surface of the pores a binder may be used or the part of the elastomer may be dissolved and resolidified to bind the coagulating substance.

As described in detail hereinabove, the vascular prosthesis of this invention is an improvement over a conventional vascular prosthesis composed mainly of a porous PTFE tubing, and also is given a high level of function, exhibiting characteristics not seen in the prior art.

While the invention has been described in detail and with reference to specific embodiments thereof, it will be apparent to one skilled in the art that various changes and modifications can be made therein without departing from the spirit and scope thereof.

What is claimed is:

1. A vascular prosthesis comprising a porous polytetrafluoroethylene tubing having a microstructure composed of fibers and nodes, said nodes being connected to one another by the fibers, said tubing containing an anti-coagulant substance and having a porous elastomer coating bonded to the exterior thereof, said porous elastomer coating containing a substance which counteracts the anti-coagulant substance.

2. The vascular prosthesis of claim 1, wherein said anti-coagulant substance is heparin or its derivative.

3. The vascular prosthesis of claim 2, wherein said haparin or derivatives thereof is contained in said PTFE tubing ionically bonded to a crosslinked polymeric amine.

4. The vascular prosthesis of claim 3, wherein said anti-coagulant is contained in said polymeric gel in an amount of about 0.2 to 5% by weight.

5. The vascular prosthesis of claim 1, wherein said counteracting substance is an inorganic or organic coagulating substance.

6. The vascular prosthesis of claim 1, wherein said counteracting substance is a heparin antagonist.

7. The vascular prosthesis of claim 6, wherein said heparin antagonist is protamine or its derivative.

8. The vasular prosthesis of claim 1, wherein said PTFE tubing has a pore diameter of about 2 to about 100 µm, a porosity of at least about 70% and a wall thickness of about 0.3 to 1.0 mm.

9. The vascular prosthesis of claim 8, wherein said porous elastomer coating has an average pore diameter of about 10 µm to about 500 µm, a thickness of about 20 to about 500 µm and a porosity of about 50 to about 95%.

10. The vascular prosthesis of claim 1, wherein said elastomer is selected from the group consisting of fluorine rubber, silicone rubber, urethane rubber, acrylic rubber, and natural rubber.

11. The vascular prosthesis of claim 10, wherein said elastomer has a porosity of about 50% to about 90%.

12. The vascular prosthesis of claim 11, wherein said elastomer coating is about 20 to about 500 µm thick.

13. The vascular prosthesis of claim 1, wherein said anti-coagulant is selected from the group consisting of polysaccharide sulfates and organic acids.

14. The vascular prosthesis of claim 13, wherein said anti-coagulant is selected from the group consisting of heparin and derivatives thereof, chondroitin sulfate, charonin sulfate, and citric acid.

15. The vascular prosthesis of claim 1, wherein said anti-coagulant is contained in said PTFE tubing dispersed in a polymeric gel.

16. The vascular prosthesis of claim 1, wherein said substance which counteracts the anti-coagulant is selected from the group consisting of silica, alumina, carbon black, activated carbon, and antagonistic agents for anti-coagulants.

17. The vascular prosthesis of claim 1, wherein said substance which counteracts the anti-coagulant is present with said elastomer in an amount of about 0.5% to about 10% by weight based on the weight of the elastomer.

* * * * *